(12) United States Patent
Matsumoto

(10) Patent No.: US 7,279,219 B2
(45) Date of Patent: Oct. 9, 2007

(54) POROUS CALCIUM PHOSPHATE CERAMIC AND METHOD FOR PRODUCING SAME

(75) Inventor: Toshio Matsumoto, Tokyo (JP)

(73) Assignee: PENTAX Corporation, Tokyo (JP)

( * ) Notice: Subject to any disclaimer, the term of this patent is extended or adjusted under 35 U.S.C. 154(b) by 139 days.

(21) Appl. No.: 10/996,434

(22) Filed: Nov. 26, 2004

(65) Prior Publication Data

US 2005/0119761 A1    Jun. 2, 2005

(30) Foreign Application Priority Data

Nov. 27, 2003   (JP)   ............................. 2003-397853

(51) Int. Cl.
B32B 3/26   (2006.01)
C04B 38/00  (2006.01)

(52) U.S. Cl. .............. 428/307.7; 428/304.4; 428/307.3; 501/80; 501/84; 424/422; 424/426; 65/21.4

(58) Field of Classification Search ............ 428/304.4, 428/307.3, 307.7; 501/80, 84; 424/422, 424/426; 65/21.4

See application file for complete search history.

(56) References Cited

U.S. PATENT DOCUMENTS 4,371,484 A  *  2/1983  Inukai et al. ................. 264/44

6,340,648 B1     1/2002  Imura et al.
2002/0114938 A1  8/2002  Matsumoto

FOREIGN PATENT DOCUMENTS

| EP | 1155705     | 11/2001 |
|----|-------------|---------|
| JP | 2000-302567 | 10/2000 |

OTHER PUBLICATIONS

English language Abstract of JP 2000-302456, Published Oct. 31, 2000.

* cited by examiner

Primary Examiner—John J. Zimmerman
Assistant Examiner—Aaron Austin
(74) Attorney, Agent, or Firm—Greenblum & Bernstein, P.L.C.

(57) ABSTRACT

A porous calcium phosphate ceramic comprising a support portion having pores, and ring-shaped portions formed in the pores, the ring-shaped portions having pluralities of fine pores so that they have a network structure. A method for producing a porous calcium phosphate ceramic comprising stirring a slurry containing coarse calcium phosphate particles, fine calcium phosphate particles, a nonionic surfactant and a water-soluble high-molecular compound to foam the slurry; gelling the foamed slurry; and then drying the resultant get to obtain a sintered porous calcium phosphate ceramic; the nonionic surfactant being malamide and/or polyoxyethylene lauryl ether.

10 Claims, 5 Drawing Sheets

POROUS CALCIUM PHOSPHATE CERAMIC AND METHOD FOR PRODUCING SAME

FIELD OF THE INVENTION

The present invention relates to a porous calcium phosphate ceramic excellent in biocompatibility and suitable for a carrier for cultivation of cells or biological tissues and for biomaterials such as artificial dental roots and bone-filling materials, and a method for producing such a porous calcium phosphate ceramic.

BACKGROUND OF THE INVENTION

Materials used for artificial bones and artificial dental roots (hereinafter referred to as "bone-filling materials") in dentistry, brain surgery, plastic surgery, orthopedic surgery, etc. are desired to have (a) no toxicity, (b) sufficient mechanical strength and (c) excellent compatibility with biological tissues.

Because porous calcium phosphate ceramics meets these conditions, they are utilized as bone-filling materials. When used as bone-filling materials, the porous calcium phosphate ceramics preferably have as high porosity as possible from the aspect of biocompatibility. However, because higher porosity leads to lower mechanical strength in the porous bodies, they cannot be used as bone-filling materials for portions needing high mechanical strength. Thus, porous calcium phosphate ceramics having both excellent biocompatibility and mechanical strength are desired.

JP 2000-302567 A discloses a sintered body comprising a body portion formed by substantially dense sintered calcium phosphate, and a surface portion formed by a finely ragged or porous sintered calcium phosphate layer. JP 2000-302567 A describes that fine raggedness or a porous sintered calcium phosphate layer on the surface of the porous sintered body increases a specific surface area, making it easy for osteoblasts to attach to the surface of the porous sintered body.

However, in order that a bone is formed in a bone-filling material embedded in a living body, bone-forming cells such as osteoblasts, etc. should be attached to the surface of the bone-filling material, and nutrition should be supplied to these cells. Even though osteoblasts were attached to the surface of the bone-filling material, a new bone would not be formed without nutrition. The sintered body of JP 2000-302567 A does not have a structure, to which proteins for forming blood vessels for sufficiently supplying nutrition to the osteoblasts are easily attached, failing to sufficiently accelerate the formation of a new bone.

The growth of blood vessels is caused by growth factors and/or inducers such as fibroblast growth factors (FGF), etc. The growth factors and/or inducers are proteins produced by cells. In order that the growth factors and/or inducers effectively function in the bone-filling material, etc., to improve the capability of the bone-filling material to form a new bone, the bone-filling material preferably has such a structure that the growth factors and/or inducers are trapped on its surface.

OBJECTS OF THE INVENTION

Accordingly, the object of the present invention is to provide a porous calcium phosphate ceramic comprising excellent new-bone-forming capability and large mechanical strength.

Another object of the present invention is to provide a method for producing such a porous calcium phosphate ceramic.

SUMMARY OF THE INVENTION

As a result of intensive study in view of the above objects, the inventor has found that (a) a porous calcium phosphate ceramic comprising a relatively dense, porous body of calcium phosphate, and ring-shaped portions having a network structure, which is formed on the walls of pores of the porous body, has excellent mechanical strength and bone-forming capability; and that (b) a porous calcium phosphate ceramic having ring-shaped portions on its pore walls is produced by foaming a slurry containing coarse calcium phosphate particles, fine calcium phosphate particles, and a malamide surfactant and/or a polyoxyethylene lauryl ether surfactant by stirring, and then gelling the slurry. The present invention has been completed based on these findings.

Thus, the porous calcium phosphate ceramic of the present invention comprises a support portion having pores, and ring-shaped portions formed in the pores, the ring-shaped portions having pluralities of fine pores so that they have a network structure.

The ring-shaped portions preferably project inward from the pore walls. The fine pores of the ring-shaped portions preferably have an average diameter of 1 to 5000 nm. The ring-shaped portions are preferably formed by fine calcium phosphate particles. The fine particles forming the ring-shaped portions preferably have an average diameter of 1 μm or less. The ring-shaped portions are preferably as thick as 1 μm or less.

The method for producing the porous calcium phosphate ceramic of the present invention comprises stirring a slurry containing coarse calcium phosphate particles, fine calcium phosphate particles, a nonionic surfactant and a water-soluble high-molecular compound to foam the slurry; gelling the foamed slurry; and then drying the resultant gel to obtain a porous sintered calcium phosphate ceramic; the nonionic surfactant being malamide and/or polyoxyethylene lauryl ether.

The coarse particles are preferably partially pulverized by stirring a dispersion of the coarse particles, to obtain the slurry containing coarse particles and fine particles. It is preferable that the coarse particles have an average particle size of 5 to 20 μm, and that the fine particles have an average particle size of 1 μm or less. The mass ratio of the coarse particles to the fine particles is preferably in a range of 1000/1 to 100000/1.

1 to 10 parts by mass of the water-soluble high-molecular compound and 1 to 10 parts by mass of the nonionic surfactant, per 100 parts by mass of the total of the coarse calcium phosphate particles and the fine calcium phosphate particles, are preferably contained in the slurry. The total concentration of the coarse particles, the fine particles, the nonionic surfactant and the water-soluble high-molecular compound is preferably 20 to 50% by mass in the slurry.

DETAILED DESCRIPTION OF THE PREFERRED EMBODIMENTS

[1] Porous Calcium Phosphate Ceramic

Figure 1:
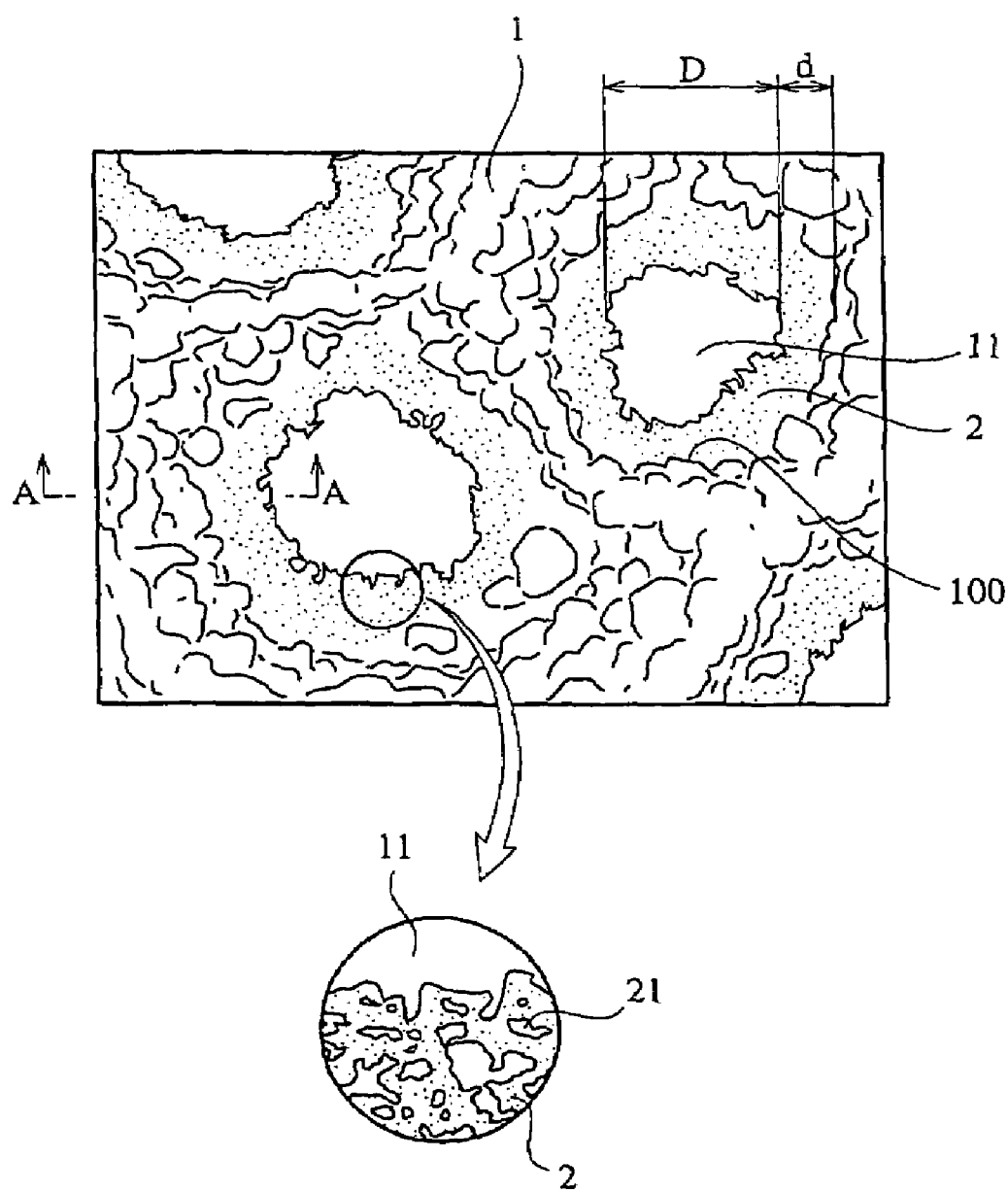
FIG. 1 is a top view showing a porous calcium phosphate ceramic of the present invention.
Figure 2:
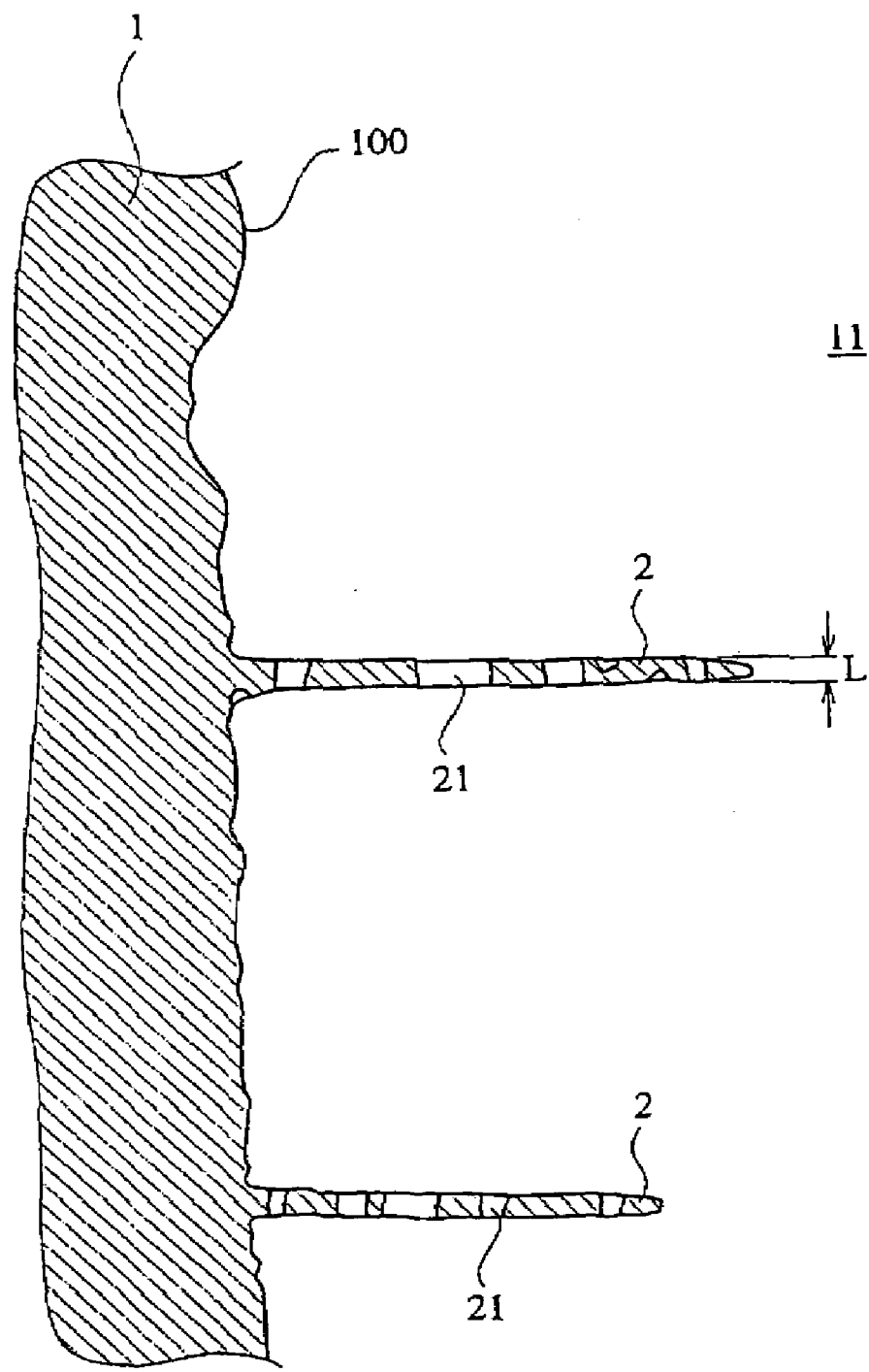
FIG. 2 is an enlarged cross-sectional view taken along the line A-A in FIG. 1.

As schematically shown in FIGS. 1 and 2, the porous calcium phosphate ceramic comprises a support portion 1 and pluralities of ring-shaped portions 2. The support portion 1 comprises pluralities of pores 11. The average of the diameters D of the pores 11 is preferably 10 to 300 μm. When the average of the pore diameters D is less than 10 μm, the pores 11 are too narrow to permit blood vessels to enter. When the average of the pore diameters D exceeds 300 μm, fibroblasts, etc. enter the pores 11 to hinder the formation of a bone.

FIG. 2 shows the longitudinal cross-section of the porous calcium phosphate ceramic. The ring-shaped portions 2 project inward from the wall 100 of the pore 11. As shown in FIG. 2, pluralities of ring-shaped portions 2 are formed in one pore 11. The ring-shaped portions 2 are preferably formed substantially perpendicularly to the wall 100 of the pore 11. Though most ring-shaped portions 2 are in a closed ring shape, some of them may be in an open ring shape because of partial defects. The ring-shaped portions 2 are preferably as wide as about 5 to 50 μm. When the width d of the ring-shaped portion 2 is less than 5 μm, there is no sufficient effect of trapping proteins for forming blood vessels, etc. When the width d exceeds 50 μm, the ring-shaped portions 2 are likely to clog the pores 11.

Because a large number of fine pores 21 having a diameter of 1 μm or less are formed in the ring-shaped portions 2, the ring-shaped portions 2 have a network structure. The fine pores 21 penetrate the ring-shaped portions 2. Each ring-shaped portion 2 preferably has a thickness L of 1 μm or less. The ring-shaped portions 2 are mainly formed by fine particles having an average diameter of 1 μm or less. The fine particles preferably do not overlap in an axial direction, so that the ring-shaped portions 2 have substantially the same thickness as the diameters of the fine particles.

The porous calcium phosphate ceramic preferably has a porosity of 60 to 95%. When the porosity is less than 60%, proteins, etc. do not easily enter into the porous calcium phosphate ceramic. When the porosity exceeds 95%, the porous calcium phosphate ceramic has insufficient mechanical strength. Because a large number of fine pores 21 are formed in the ring-shaped portions 2 as described above, the ring-shaped portions 2 are very porous. On the other hand, the wall 100 of the support portion 1 having the pores 11 is relatively dense. The ring-shaped portions 2 thus have a structure to permit a body fluid to pass easily, while the support portion 1 has a structure with a large mechanical strength.

When the porous calcium phosphate ceramic is embedded in a living body, the pores 11 in the support portion 1 are filled with a body fluid. Because the ring-shaped portions 2 having a network structure are contained in the pores 11, the fine pores 21 of the ring-shaped portion 2 are also filled with a body fluid. Proteins for forming or inducing blood vessels, which are contained in the body fluid, are trapped in the fine pores 21. Further, precursor cells (stem cells) of osteoblasts are attached to the pores 11 of the porous calcium phosphate ceramic through the ring-shaped portions 2. Because the precursor cells of the osteoblasts are generally as small as several micrometers, they can enter into the pores 11 of the support portion 1. With the bone-forming proteins supplied, the precursor cells are differentiated into osteoblasts, forming a bone. When osteoblasts are attached to the pore 11 through the ring-shaped portions 2, the bone-forming proteins are easily supplied to the osteoblasts, accelerating the formation of blood vessels and/or a bone in the pores 11.

[2] Production Method of Porous Calcium Phosphate Ceramic (1) Materials

Materials for the porous calcium phosphate ceramic are coarse calcium phosphate particles, fine calcium phosphate particles, a nonionic surfactant, and a water-soluble high-molecular compound. The terms "coarse particles" and "fine particles" used herein mean particles with relatively different sizes. The coarse particles generally have an average particle size of more than 1 μm, and the fine particles generally have an average particle size of 1 μm or less.

(a) Coarse Particles

It is preferable that the coarse particles are made of calcium phosphate and have an average particle size of 5 to 20 μm. The atomic ratio of Ca/P in calcium phosphate is preferably 1.5 to 1.7. When the atomic ratio of Ca/P is less than 1.5, the porous calcium phosphate ceramic has too small biocompatibility. When the atomic ratio of Ca/P is more than 1.7, the porous calcium phosphate ceramic contains too much calcium to have biocompatibility. A preferable example of calcium phosphate is hydroxyapatite. The coarse particles mainly constitute the support portion 1 of the porous calcium phosphate ceramic.

The coarse calcium phosphate particles may be formed by a usual wet method. A synthesis reaction may be carried out in a uniform or non-uniform system. The specific surface area of the coarse calcium phosphate particles is preferably 30 to 300 $m^2/g$, more preferably 50 to 200 $m^2/g$. When the specific surface area is less than 30 $m^2/g$, the coarse particles are too large to form the ring-shaped portions. Coarse calcium phosphate particles having a specific surface area of more than 300 $m^2/g$ are difficult to produce by the present technologies. The uniform synthesis reaction can produce coarse calcium phosphate particles having a specific surface area of about 100 to 300 $m^2/g$, and the non-uniform synthesis reaction can produce coarse calcium phosphate particles having a specific surface area of about 30 to 100 $m^2/g$.

(b) Fine Calcium Phosphate Particles

The fine calcium phosphate particles preferably have an average diameter of 1 μm or less, more preferably 10 to 500 nm, most preferably 10 to 200 nm. When the average particle size exceeds 1 μm, the ring-shaped portions 2 are too thick to form the fine pores 21.

The atomic ratio of Ca to P in the fine particles may be the same as or different from that in the coarse particles. When the atomic ratio of Ca to P in the fine particles is substantially the same as that of the support portion, the porous calcium phosphate ceramic embedded in a living body is relatively stable. The dissolving of a porous calcium phosphate ceramic stable in a living body takes so much time that it may function as a support for cells, etc. for a relatively long period of time. What is meant by "substantially the same atomic ratio of Ca to P as that of the coarse particles" is that the atomic ratio of Ca to P in the fine particles is 95 to 105% of that in the coarse particles. The fine particles mainly constitute the ring-shaped portions 2 in the porous calcium phosphate ceramic. When the atomic ratio of Ca to P is different from that of the coarse particles, the atomic ratio of Ca to P of the fine particles is preferably lower than that of the coarse particles and 1.4 or more. When it is lower than the atomic ratio of Ca to P of the coarse particles, the fine particles are so likely to be reacted with a body fluid that the ring-shaped portion 2 are easily dissolved. When the atomic ratio of Ca to P in the fine particles is lower than 1.4, the fine particles are taken into the coarse particles during sintering.

The production method of the fine particles is the same as in the coarse particles. When the fine particles having the same atomic ratio of Ca to P as in the coarse particles are used, the fine particles may be obtained by partially pulverizing the coarse particles. The fine particles preferably have a specific surface area of 80 to 300 $m^2/g$.

(c) Nonionic Surfactant

As a nonionic surfactant, malamide and/or polyoxyethylene lauryl ether are used. The malamide surfactant and the polyoxyethylene lauryl ether surfactant are interacted specifically with calcium phosphate. Specifically, the surfactant is bonded to calcium in the calcium phosphate so that it covers the particles. This makes it easy for the coarse calcium phosphate particles and the fine calcium phosphate particles to be dispersed in the slurry without agglomeration.

The malamide surfactant is available, for instance, from Lion Corporation. The polyoxyethylene lauryl ether surfactant is available, for instance, from Nikko Chemicals, Co., Ltd.

(d) Water-Soluble High-Molecular Compound

The water-soluble high-molecular compound in a state of an aqueous solution or dispersion is turned to a gel by heating, etc. The aqueous solution or dispersion includes any of an aqueous solution, a colloidal solution, an emulsion and a suspension. Examples of such water-soluble high-molecular compounds include cellulose derivatives such as methylcellulose and carboxymethylcellulose; polysaccharides such as curdlan; synthetic polymers such as polyvinyl alcohol, polyacrylic acid, polyacrylamide and polyvinyl pyrrolidone, etc. Preferred among them is methylcellulose.

(2) Preparation of Slurry

The coarse calcium phosphate particles and water are mixed and stirred by an impeller-type homogenizer, etc. This stirring partially pulverizes the coarse particles to fine particles. Examples of the impeller-type homogenizer include PH91, PA92, HF93, FH94P, PD96 and HM10 available from SMT Co., Ltd., etc. Though the stirring period may depend on the stirring power, it is generally 1 to 30 minutes. The stirring power means "[maximum output of stirring apparatus (W)/amount of slurry (L)]×(actual number of rotation/maximum number of rotation)." For instance, when the coarse calcium phosphate particles and water are stirred at 240 W/L for 5 minutes, approximately 1% of the coarse particles are pulverized to particles having a diameter of 1 μm or less. The mass ratio of the coarse particles to the fine particles is preferably in a range of 1,000/1 to 100,000/1. Though the coarse particles and the fine particles may be prepared separately, the fine particles are more preferably obtained by partially pulverizing the coarse particles because the fine particles are unlikely to aggregate together.

Subsequently, the nonionic surfactant and the water-soluble high-molecular compound are added and stirred to obtain a slurry. The slurry preferably contains 1 to 10 parts by mass of the water-soluble high-molecular compound, 1 to 10 parts by mass of the nonionic surfactant, and 100 parts by mass, in total, of coarse particles and fine particles. When the total amount of the calcium phosphate particles is too small in the slurry, drying the gel takes a relatively long period of time. On the other hand, too much an amount of the total calcium phosphate particles leads to a high-viscosity slurry, which is difficult to be foamed. Further, the gelation of the slurry is difficult when the water-soluble high-molecular compound is less than 1 part by mass, and more than 10 parts by mass of the water-soluble high-molecular compound provides a high-viscosity slurry, which is difficult to be foamed. The water-soluble high-molecular compound is more preferably 1 to 5 parts by mass per 100 parts by mass of the total calcium phosphate particles. When the nonionic surfactant is less than 1 part by mass, the slurry cannot easily be foamed. Even though the nonionic surfactant exceeds 10 parts by weight, further improved effect cannot be obtained. The nonionic surfactant is more preferably 1 to 5 parts by mass per 100 parts by mass of the total calcium phosphate particles.

The total concentration of the coarse calcium phosphate particles, the fine calcium phosphate particles, the water-soluble high-molecular compound and the nonionic surfactant is preferably 20 to 50% by mass based on 100% by mass of the slurry. When the above total concentration is less then 20% by mass, drying takes too long a period of time after gelation, and the resultant gel is often crushed after drying, failing to maintain the porous structure. On the other hand, when the above total concentration is more then 50% by mass, the viscosity of the slurry is too high to foam by stirring. The above total concentration is more preferably 25 to 40% by mass.

(3) Foaming

When the slurry is vigorously stirred, it is foamed while taking air. As an apparatus for vigorous stirring, an impeller-type homogenizer may be used. Although the impeller-type homogenizer is generally designed not to foam the slurry, etc., the slurry can be remarkably foamed if the stirring power is 50 W/L or more. A preferred stirring apparatus comprises disc-shaped stirring blades having saw-blade-like projections on their circumferences, and baffle plates disposed on an inner wall of a stirring chamber. A preferred example of the impeller-type homogenizer is the same as used in the above pulverization of the coarse particles.

To further accelerate foaming, it is preferable to introduce air, an inert gas such as nitrogen, argon, etc. into the slurry while stirring. When air, etc. are introduced into the slurry, the stirring power of about 20 W/L is sufficient.

Though depending on the stirring power, the stirring time may be approximately 1 to 30 minutes. To produce fine, uniform and stable air bubbles, a stirring temperature (temperature of the slurry) is preferably relatively low, specifically about 0 to 25° C., particularly 5 to 20° C.

Stirring provides the slurry with as small air bubbles as micrometers. The lightweight, fine particles gather on the interfaces of the slurry with the air bubbles to form a layer of fine particles, while the heavyweight, coarse particles are concentrated inside the slurry walls. It is considered that such orientation of the fine calcium phosphate particles occurs locally near the surface because the fine particles are lighter than the coarse particles. Such localization requires that the coarse particles and the fine particles are well dispersed in the slurry. It is thus indispensable that malamide and polyoxyethylene lauryl ether are used as the surfactant. Other surfactants than malamide and polyoxyethylene lauryl ether do not improve the dispersibility of the fine particles, etc., failing to cause such localization of the fine particles.

When the slurry containing air bubbles is gelled, dried and sintered, the coarse particles gathering inside the slurry walls form the support portion 1, and the fine particles form the ring-shaped portions 2. The use of the malamide surfactant and/or the polyoxyethylene lauryl ether surfactant thus makes it possible to produce a porous calcium phosphate ceramic comprising the support portion 1 and the ring-shaped portions 2 formed on the walls of the pores 11.

The foamed slurry is preferably cast in a mold lined with a flexible water-resistant film. The flexible water-resistant film easily peels off from the mold due to drying shrinkage of the ceramic, thereby preventing the deformation of the ceramic on a surface in contact with the mold or the cracking of an inner portion of the ceramic, to provide a high-quality dried body.

(4) Gelation

The foamed slurry is heated at 80 to 95° C. When the slurry is heated, gelation occurs by the action of the water-soluble high-molecular compound. After gelation, the air bubbles do not substantially disappear. The fine particles gathering near the interfaces of air bubbles are thus gelled near the interfaces.

(5) Drying

The resultant gel is dried by keeping the gel preferably at such a high temperature that water does not boil, for example, 80° C. or higher and lower than 100° C. When water boils, the air bubbles are likely to disappear. When the gel is dried at such a high temperature that water does not boil, the gel shrinks substantially isotropically, whereby the air bubbles remain unchanged without cracking, etc.

(6) Cutting

Because the water-soluble high-molecular compound in the dried body acts as a binder, the dried body has sufficient mechanical strength for handling. Thus, the dried body can be cut or worked to a desired shape without calcining.

(7) Degreasing

The dried body may be degreased to remove the water-soluble high-molecular compound and the nonionic surfactant, if necessary. The degreasing of the dried body may be carried out at 300 to 900° C.

(8) Sintering

The dried body is preferably sintered at 1000 to 1250° C. When the sintering temperature is lower than 1000° C., the resultant porous calcium phosphate ceramic has insufficient strength. On the other hand, when the sintering temperature is higher than 1250° C., too many ring-shaped portions disappear. Though the sintering period may be selected properly depending on the sintering temperature, it is generally about 2 to 10 hours. Gradual heating of the dried body to the predetermined sintering temperature makes it possible to degrease the dried body. For example, the dried body is heated from room temperature to about 600° C. at a rate of about 10 to 100° C./hour, and then heated to the sintering temperature at a rate of about 50 to 200° C./hour, and kept at the sintering temperature. After the completion of sintering, it may be cooled slowly.

Though pores shrink to about 70% of those before sintering by removing the water-soluble high-molecular compound and the surfactant by sintering, coarse and/or fine calcium phosphate particles are fused together while keeping the structure of the dried body. Only fine particles are left in the fine-particle layer in the pores, thereby turning the fine-particle layer to a network structure. Thus, a porous calcium phosphate ceramic comprising a support portion having pores and ring-shaped portions having a network structure formed in the pores can be obtained.

The present invention will be explained in more detail referring to Examples below without intention of restricting the scope of the present invention.

EXAMPLE 1

100 parts by mass of hydroxyapatite powder having an average diameter of 15 μm and 263 parts by mass of water were mixed and stirred in a homogenizer PA92 available from SMT Co., Ltd, such that the hydroxyapatite powder was partially pulverized to fine hydroxyapatite particles having an average diameter of 0.5 μm, thereby forming a dispersion containing the coarse hydroxyapatite particles and the fine hydroxyapatite particles. The mass ratio of the coarse particles to the fine particles in the dispersion was about 1000 to 1. A 3%-by-mass malamide surfactant solution available from Lion Corporation and 67 parts by mass of a 10%-by-mass methylcellulose solution were then added to obtain a slurry containing 1% by mass of the malamide surfactant. The slurry was foamed by vigorous stirring by the homogenizer for 5 minutes under a stirring power of 60 W/L (output during stirring), while keeping the temperature of the slurry at 8° C.

The resultant slurry containing air babbles was introduced into a mold and heated at 83° C. for 2 hours to produce a gel. The gel was dried at 83° C.

The resultant dried body was heated from room temperature to 600° C. at a rate of 50° C./hour in the air, heated to 1200° C. at a rate of 100° C./hour, sintered at 1200° C. for 4 hours, cooled down to 600° C. at a rate of 50° C./hour, kept at 600° C. for 4 hours, and cooled down to room temperature at a rate of 100° C./hour, to produce a porous sintered hydroxyapatite ceramic.

Figure 3:
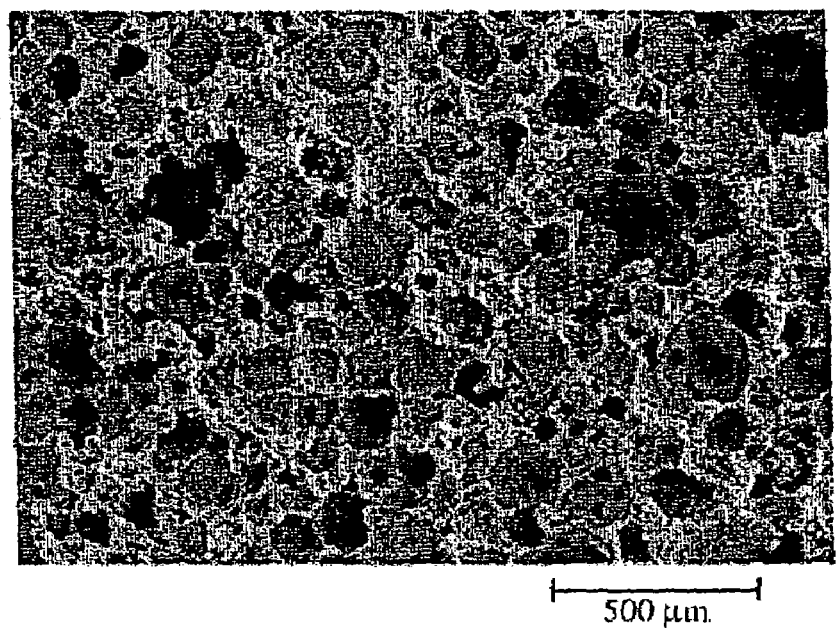
FIG. 3 is a scanning electron photomicrograph of the porous hydroxyapatite ceramic in Example 1.
Figure 4:
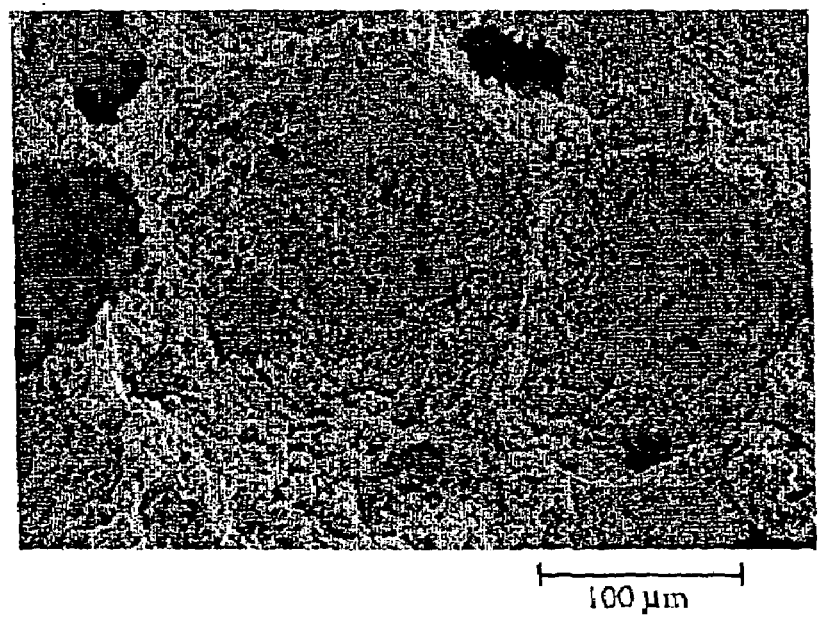
FIG. 4 is another scanning election photomicrograph of the porous hydroxyapatite ceramic in Example 1.

The porosity of the porous sintered hydroxyapatite ceramic was 85%. FIGS. 3 and 4 are scanning electron photomicrographs of the porous hydroxyapatite ceramic. As is clear from FIGS. 3 and 4, the ring-shaped portions having a network structure were formed in the pores of the support portion, and the porous hydroxyapatite ceramic had a uniform pore size distribution mostly in a range of 50 to 500 μm. The ring-shaped portions were as thick as about 1 μm or less, and the fine pores had an average diameter of about 800 nm.

EXAMPLE 2

Figure 5:
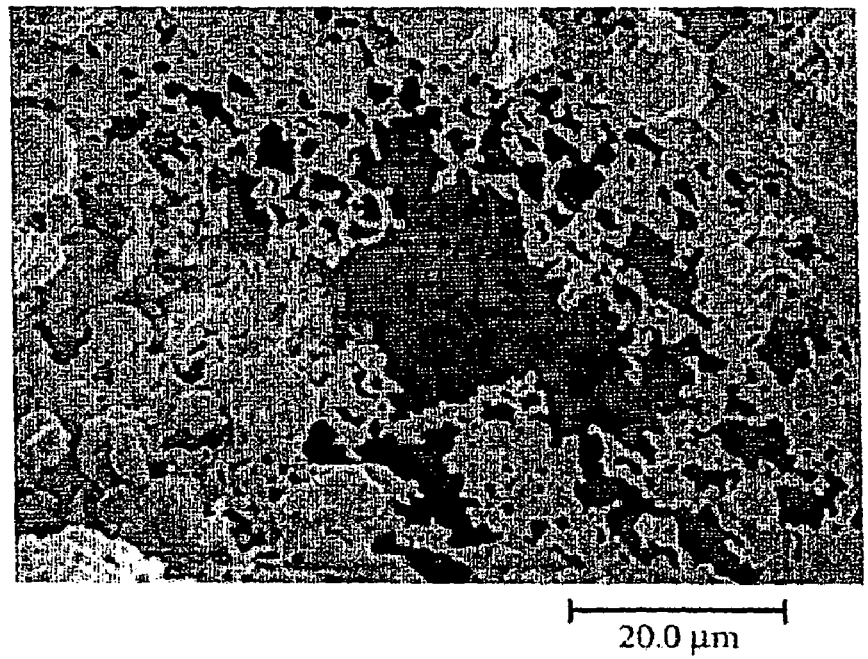
FIG. 5 is a scanning electron photomicrograph of the porous hydroxyapatite ceramic in Example 2.
Figure 6:
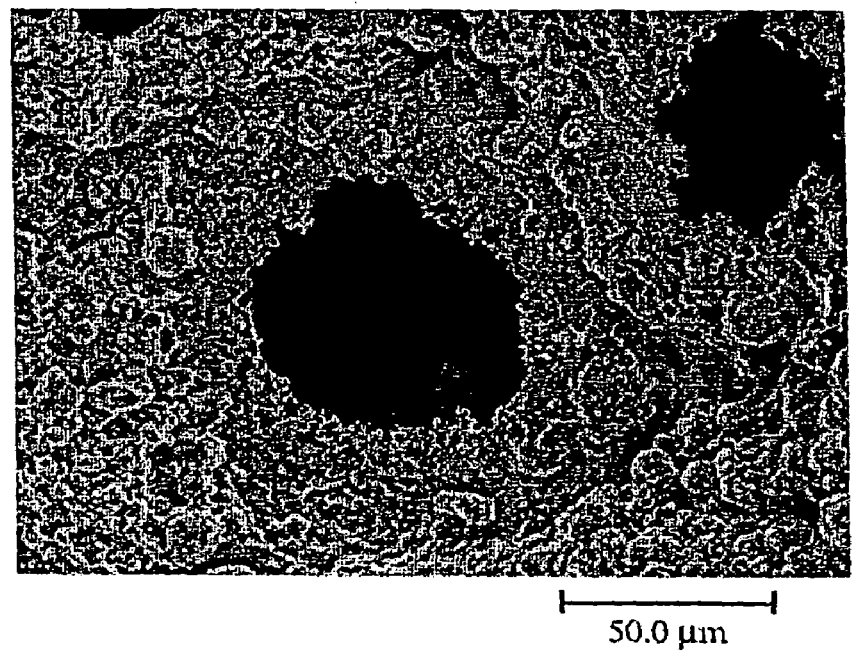
FIG. 6 is another scanning electron photomicrograph of the porous hydroxyapatite ceramic in Example 2.

A porous hydroxyapatite ceramic was produced in the same manner as in Example 1, except that 67 parts by mass of a 10%-by-mass methylcellulose solution and 3 parts by mass of polyoxyethylene lauryl ether surfactant (TEALS, available from Nihon Surfactant Kogyo K.K.) were added to a dispersion containing the coarse hydroxyapatite particles and the fine hydroxyapatite particles. The porous sintered hydroxyapatite ceramic had a porosity of 88%. FIGS. 5 and 6 are scanning electron photomicrographs of the porous hydroxyapatite ceramic. As is clear from FIGS. 5 and 6, the porous hydroxyapatite ceramic had a uniform pore size distribution mostly in a range of 50 to 500 μm. The ring-shaped portions were as thick as about 1 μm or less, and the fine pores had an average diameter of about 800 nm.

EXAMPLE 3

Figure 7:
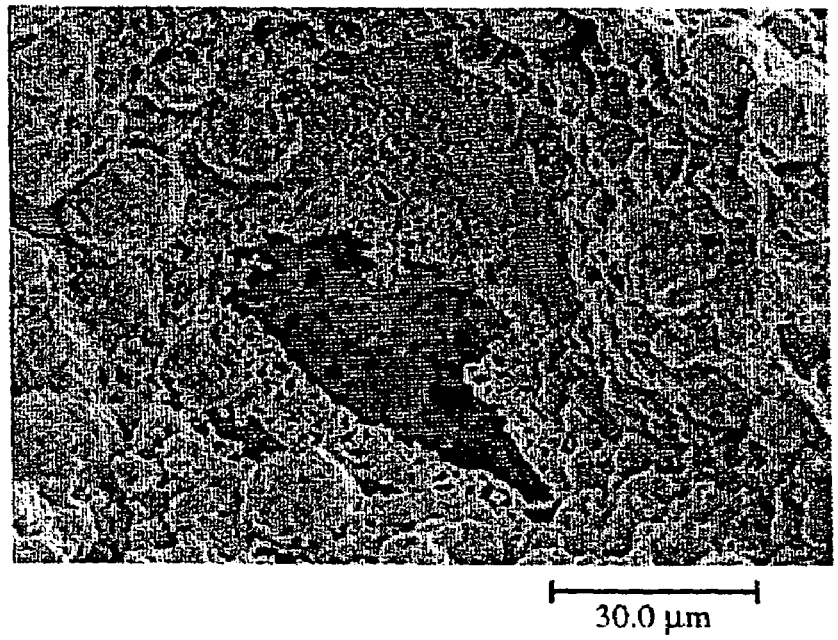
FIG. 7 is a scanning electron photomicrograph of the porous hydroxyapatite ceramic in Example 3.

A porous hydroxyapatite ceramic was produced in the same manner as in Example 1, except that 100 parts by mass of coarse hydroxyapatite particles having an average diameter of 15 μm, 0.1 parts by mass of fine hydroxyapatite particles having an average diameter of 100 nm and 263 parts by mass of water were mixed to obtain a dispersion, and that 67 parts by mass of a 10%-by-mass methylcellulose solution and 3 parts by mass of a polyoxyethylene lauryl ether surfactant (TEALS, available from Nihon Surfactant Kogyo K.K.) were added to the dispersion. The porous sintered hydroxyapatite ceramic had a porosity of 88%. FIG. 7 is a scanning electron photomicrograph of the porous hydroxyapatite ceramic. As is clear from FIG. 7, the porous hydroxyapatite ceramic had a uniform pore size distribution mostly in a range of 50 to 500 μm. The ring-shaped portions were as thick as about 1 μm or less, and the fine pores had an average diameter of about 800 nm.

COMPARATIVE EXAMPLE 1

Figure 8:
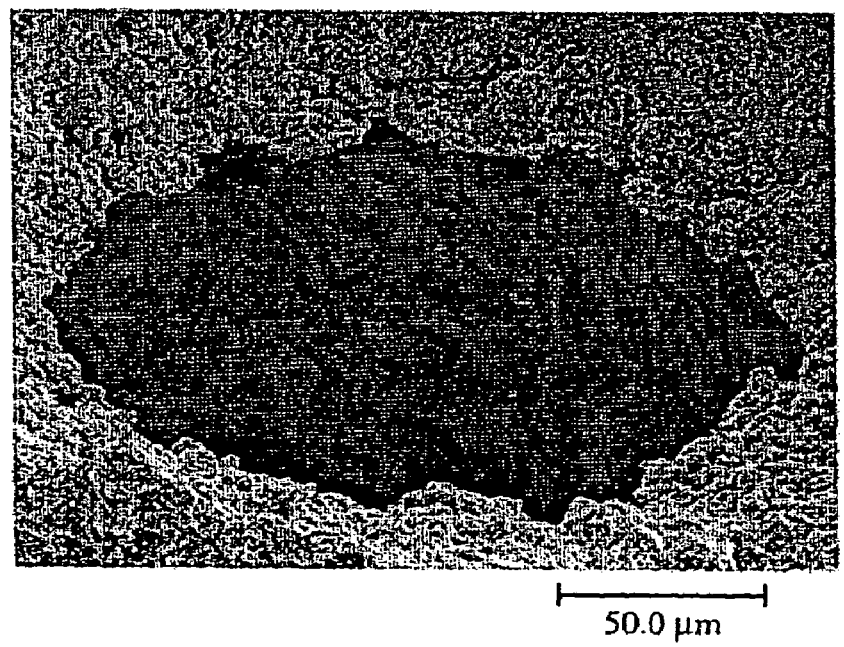
FIG. 8 is a scanning electron photomicrograph of the porous hydroxyapatite ceramic in Comparative Example 1.

A porous hydroxyapatite ceramic was produced in the same manner as in Example 1, except that 10 parts by mass (on a solid basis) of N,N-dimethyldodecylamine oxide ["AROMOX™," available from Lion Corporation] as a fatty acid alkanolamide surfactant was added in addition to a binder to a dispersion containing the coarse hydroxyapatite particles and the fine hydroxyapatite particles. The porosity of the porous sintered hydroxyapatite ceramic was 85%. FIG. 8 is a scanning electron photomicrograph of the porous hydroxyapatite ceramic. As is clear from FIG. 8, fine pores were distributed throughout this porous hydroxyapatite ceramic, which did not have a structure composed of the support portion and the ring-shaped portions.

The porous calcium phosphate ceramic of the present invention comprises the support portion having pores, and the ring-shaped portions formed in the pores of the support portion. Because the ring-shaped portions have as fine pores as nanometers so that they have a network structure, bone-forming proteins easily enter into the ring-shaped portions to have osteoblasts when the porous calcium phosphate ceramic is embedded in a living body. Also, the porous walls of the support portion are relatively dense with sufficient mechanical strength as a whole. The porous calcium phosphate ceramic having such excellent bone-forming capability and mechanical strength is suitable as bone-filling materials, etc.

The method of the present invention provides a porous calcium phosphate ceramic having excellent bone-forming capability and mechanical strength. The production method of the present invention, which comprises foaming a slurry containing coarse calcium phosphate particles, fine calcium phosphate particles, a nonionic surfactant and a water-soluble high-molecular compound; and gelling the foamed slurry, uses malamide and/or polyoxyethylene lauryl ether as the nonionic surfactant. The fine calcium phosphate particles in the slurry are concentrated on the pore surfaces by the action of the malamide surfactant and/or the polyoxyethylene lauryl ether surfactant. Thus, the production method of the present invention is an extremely easy method for orienting calcium phosphate particles by using a particular nonionic surfactant.

The present disclosure relates to subject matter contained in Japanese Patent Application No. 2003-397853 (filed on Nov. 27, 2003) which is expressly incorporated herein by reference in its entirety.

What is claimed is:

1. A porous calcium phosphate ceramic comprising a support portion having pores including walls, and ring-shaped portions formed on the walls of said pores and projecting inwardly from the walls of said pores, said support portion and said ring-shaped portions comprising calcium phosphate ceramic, and said ring-shaped portions including a plurality of fine pores forming a network structure in said ring-shaped portion.

2. The porous calcium phosphate ceramic according to claim 1, wherein said fine pores have an average diameter of 1 to 5000 nm.

3. The porous calcium phosphate ceramic according to claim 1, wherein said ring-shaped portions are formed by fine calcium phosphate particles.

4. The porous calcium phosphate ceramic according to claim 1, wherein said ring-shaped portions are as thick as 1 μm or less.

5. A method for producing a porous calcium phosphate ceramic comprising a support portion having pores including walls, and ring-shaped portions formed on the walls of said pores and projecting inwardly from the walls of said pores, said support portion and said ring-shaped portions comprising calcium phosphate ceramic, and said ring-shaped portions including a plurality of fine pores forming a network structure in said ring-shaped portion, said method comprising stirring a slurry containing coarse calcium phosphate particles, fine calcium phosphate particles, a nonionic surfactant and a water-soluble high-molecular compound to foam said slurry; gelling the resultant foamed slurry; and then drying the resultant gel to obtain a porous sintered calcium phosphate ceramic; said nonionic surfactant being malamide and/or polyoxyethylene lauryl ether.

6. The method for producing a porous calcium phosphate ceramic according to claim 5, wherein said coarse particles are partially pulverized by stirring a dispersion of said coarse particles, to obtain said slurry containing coarse particles and fine particles.

7. The method for producing a porous calcium phosphate ceramic according to claim 5, wherein the mass ratio of said coarse particles to said fine particles is 1000/1 to 100000/1.

8. The method for producing a porous calcium phosphate ceramic according to claim 5, wherein said coarse particles have an average particle size of 5 to 20 μm, and said fine particles have an average particle size of 1 μm or less.

9. The method for producing a porous calcium phosphate ceramic according to claim 5, wherein 1 to 10 parts by mass of said water-soluble high-molecular compound and 1 to 10 parts by mass of said nonionic surfactant are added to 100 parts by mass, in total, of said coarse particles and said fine particles.

10. The method for producing a porous calcium phosphate ceramic according to claim 5, wherein the total concentration of said coarse particles, said fine particles, said nonionic surfactant and said water-soluble high-molecular compound is 20 to 50% by mass in said slurry.

* * * * *